US010670595B2

United States Patent
Gombrich et al.

(10) Patent No.: US 10,670,595 B2
(45) Date of Patent: Jun. 2, 2020

(54) SYSTEM, METHOD AND KIT FOR DETECTION OF ANALYTES BY PRODUCTION OF ELECTROCHEMICAL SPECIES

(71) Applicant: OncoGenesis Inc., Morgan Hill, CA (US)

(72) Inventors: Peter P. Gombrich, Salinas, CA (US); Nam W. Kim, San Jose, CA (US); Christopher E. Todd, Campbell, CA (US)

(73) Assignee: OncoGenesis, Inc., Morgan Hill, CA (US)

( * ) Notice: Subject to any disclaimer, the term of this patent is extended or adjusted under 35 U.S.C. 154(b) by 0 days.

(21) Appl. No.: 15/576,572

(22) PCT Filed: May 26, 2016

(86) PCT No.: PCT/US2016/034433
§ 371 (c)(1),
(2) Date: Nov. 22, 2017

(87) PCT Pub. No.: WO2016/191603
PCT Pub. Date: Dec. 1, 2016

(65) Prior Publication Data
US 2018/0164300 A1     Jun. 14, 2018

Related U.S. Application Data

(60) Provisional application No. 62/166,593, filed on May 26, 2015.

(51) Int. Cl.
*G01N 33/543* (2006.01)
*G01N 33/574* (2006.01)

(52) U.S. Cl.
CPC ... *G01N 33/5438* (2013.01); *G01N 33/57484* (2013.01); *G01N 2333/90* (2013.01); *G01N 2800/32* (2013.01); *G01N 2800/50* (2013.01); *G01N 2800/7028* (2013.01); *G01N 2800/7095* (2013.01)

(58) Field of Classification Search
CPC .................... G01N 33/5438; G01N 33/57484
See application file for complete search history.

(56) References Cited

U.S. PATENT DOCUMENTS 5,639,626 A * 6/1997 Kiaei ................. G01N 33/5306
435/6.1
2001/0042693 A1* 11/2001 Onitskansky .......... G01N 27/49
205/780

(Continued)

*Primary Examiner* — Melanie Brown
(74) *Attorney, Agent, or Firm* — Patterson + Sheridan, LLP

(57) ABSTRACT

Systems and methods for detection of analytes by production of electrochemical species are provided. Some embodiments of this invention relate generally to carbon biosensors for detecting an analyte in a biological sample. More specifically, this invention relates generally to immunoassays for detection of analytes utilizing electroactive compounds, and more particularly, relates to diagnostic assays based on signals from electroactive chemical undergoing redox cycling on electrosensor consisting of carbon, to detect analytes wherein a precomplex mixture is formed and a multi-step, or single-step, assay is performed, resulting in greater signal.

8 Claims, 1 Drawing Sheet

(56) References Cited

U.S. PATENT DOCUMENTS

| | | | | |
|---|---|---|---|---|
| 2002/0058279 | A1* | 5/2002 | Fritsch | B01F 13/0077 |
| | | | | 435/6.12 |
| 2002/0076690 | A1* | 6/2002 | Miles | G01N 33/5438 |
| | | | | 435/5 |
| 2002/0086443 | A1* | 7/2002 | Bamdad | B82Y 30/00 |
| | | | | 436/526 |
| 2007/0105119 | A1* | 5/2007 | Gao | B82Y 15/00 |
| | | | | 435/6.11 |
| 2008/0038749 | A1* | 2/2008 | Fleischer | G01N 33/5438 |
| | | | | 435/7.1 |
| 2011/0177530 | A1* | 7/2011 | Corcoran | G01N 33/54366 |
| | | | | 435/7.92 |
| 2011/0189705 | A1* | 8/2011 | Gao | G01N 33/54306 |
| | | | | 435/7.92 |
| 2017/0212116 | A1* | 7/2017 | Braga | G01N 33/54346 |

* cited by examiner

SYSTEM, METHOD AND KIT FOR DETECTION OF ANALYTES BY PRODUCTION OF ELECTROCHEMICAL SPECIES

CROSS REFERENCE TO RELATED APPLICATIONS

This patent application is a United States National Stage Application filed under 35 U.S.C. § 371 of International Application No. PCT/US2016/034433, entitled "System, Method And Kit For Detection Of Analytes By Production Of Electrochemical Species" which was filed on May 26, 2016 which claims the benefit of, and priority to, U.S. Provisional Patent Application Ser. No. 62/166,593 filed on May 26, 2015, the disclosure of which is hereby incorporated by reference in its entirety.

FIELD

This disclosure relates generally to systems, methods and kits for detection of analytes by production of electrochemical species. Some embodiments of this invention relate generally to carbon biosensors for detecting an analyte in a biological sample. More specifically, some embodiments provide immunoassays for detection of analytes utilizing electroactive compounds, and more particularly, relates to diagnostic assays based on signals from electroactive chemical undergoing redox cycling on electrosensor comprised of carbon, to detect analytes wherein a precomplex mixture is formed and a multi-step, or single-step, assay is performed, resulting in greater signal.

BACKGROUND

Sensitive and selective detection of redox active substances, including those produced by pathogenic microorganisms, has important implications for both medical and environmental research, and in microbial fuel cells (Zhang et al., 2005, Curr Opin Microbiol 8, 276-281; Jacob et al., 2011, Current Opinion in Chem Biol 15, 149-155; Dietrich et al., 2008, Science 321, 1203-1206; and Ren et al., 2012, Microfluid Nanofluid 13, 353-381). A variety of amperometric and potentiometric techniques can be utilized to obtain information about the chemical composition of a solution (Pihel et al., 1995 Anal Chem, 67, 4514-4521; Buck et al., 2001, Anal Chem, 73, 88-97; Hengstenberg et al., 2001, Angew Chem Int Ed Engl, 40, 905-908; Muller et al., 1981, Neuro Meth, 1981, 4, 39-52), and may be used for development of the sensors for detecting redox active substances.

Electrochemical detection offers several advantages over other sensing schemes, such as fast analysis time, ease of use, and low limits of detection (Cheng et al., 2007, Electrophoresis 28, 1579-1586; Zou et al., 2008, IEEE Sens J 8, 527-535; Zevenbergen et al., 2007, Nano Lett 7, 384-388). Low-fabrication cost microscale electrochemical systems which have smaller sample volume requirements are attractive for the detection of molecules by this method. (Ino et al., 2011, Lab Chip 11, 385-388; Hwang et al., 2009, IEEE Sens J 9, 609-615).

Each of the amperometric and potentiometric techniques requires a stable reference electrode to provide accurate measurements. With the emergence of microfabrication techniques, miniaturized electrochemical sensors are now being developed and integrated inside fluidic systems (Lewis et al., 2010, Anal Chem, 82, 1659-1668; Kwakye et al., 2006 Biosens Bioelectron, 21, 2217-2223; Swensen, et al., 2009, J Am Chem Soc, 131, 4262-4266; Wang et al., 2008, Sensors, 8, 2043-2081; Straver, et al., 2012, Lab Chip, 12, 1548-1553).

Highly ordered graphite as well as hard and soft carbons are used extensively as the negative electrodes of commercial Lithium (Li) ion batteries. The high energy density values reported for these Li batteries are generally based on the performance of larger cells with capacities of up to several ampere-hours. One approach to overcome the size and energy density deficiencies in current two dimensional (2D) microbatteries is to develop three dimensional (3D) battery architectures based on specially designed arrays composed of high aspect ratio three dimensional (3D) electrode elements. For example, a micro 3D battery which has electrode arrays with a 50:1 aspect ratio (height/width), the expected capacity may be 3.5 times higher and the surface area 350 times higher than for a conventional 2D battery design.

Despite advancements in sensor technology, many challenges and significant need remains for the development of new systems and methods, particularly in the medical device and cancer diagnosis fields.

SUMMARY

This application provides systems, methods and kits for determining the presence of an analyte in a test sample by specific carbon-based biosensor that measures electrical signals from electrochemical undergoing redox cycling, which method comprises: (a) addition of a sample to an assay structure having at least one carbon electrode and an analyte binding material, (b) allowing an analyte in said sample to bind to said analyte binding material in said assay structure, (c) addition of an analyte binding molecule having a tag attached wherein said tags includes an electroactive species capable of generating a current by either accepting or transmitting one or more electrons to the at least one electrode and wherein said tag may be reacted with a substrate such that it releases the electroactive species, and (d) measuring a current through said assay structure by means of the at least one electrode within the assay structure thereby quantitating or detecting the presence or absence of the analyte.

In one embodiment, a signal from the assay structure is detected in two separate chambers for reaction and detection. This format allows higher signal amplification and cleaner signal.

In another embodiment, a signal from the assay structure is detected in a single chamber that provides both reaction and detection. This format allows more simple assay and instrument design by allowing both reaction and detection be performed in a single homogeneous environment.

In some embodiments, the electroactive species may be selected from the group consisting of p-aminophenol, 2,3-diaminophenazine, and [Ru(bpy)2LL']2+(bpy = 2,2'-bipyridine, LL'=pyrim=phenylpyridin-2-ylmethylene-amine). A preferred electroactive species is 2,3-diaminophenazine that is released by enzymatic action of horseradish peroxidase of o-phenylenediamine substrate.

In another aspect, systems or devices including an electrode assembly within a microfluidic channel are provided for electrochemical measurement of the concentration of a redox active substance. Also provided are methods of fabricating the devices and methods of measuring a concentration of a redox active substance using the devices. The devices and methods, and sensors embodying them, provide fast and sensitive detection of the presence of an analyte by detecting a redox active substance produced by the assay structure. In some embodiments, 3D electrodes with high surface area constructed with carbon matrix to detect electrochemical signal in redox cycling are provided for detection of various types of analytes in medical devices.

BRIEF DESCRIPTION OF THE FIGURES

Other aspects, embodiments and advantages of the invention will become apparent upon reading of the detailed description of the invention and the appended claims provided below, and upon reference to the drawings in which:

DETAILED DESCRIPTION

The following description sets forth exemplary methods, parameters and the like. It should be recognized, however, that such description is not intended as a limitation on the scope of the present disclosure but is instead provided as a description of exemplary embodiments.

Figure 1:
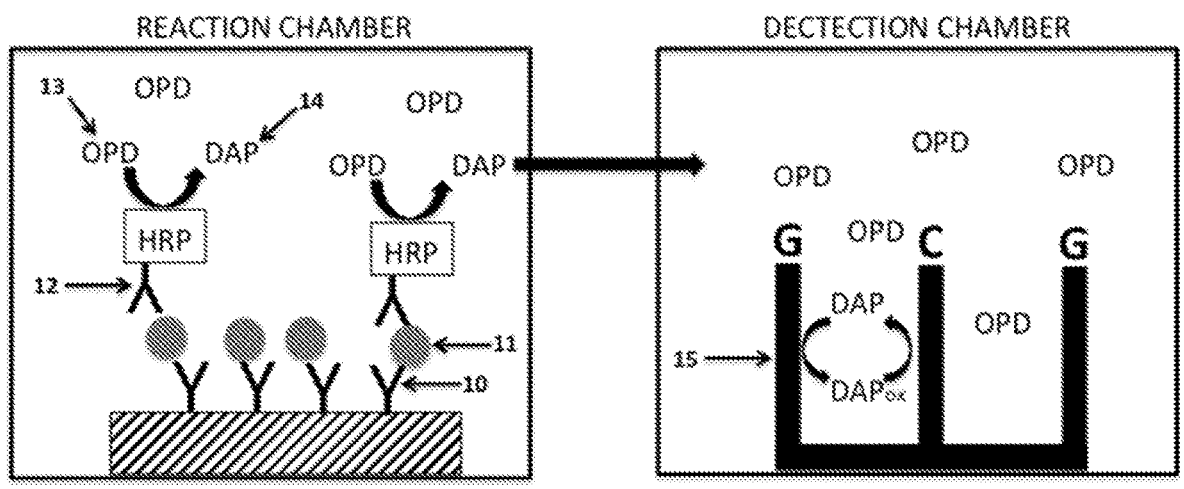
FIG. 1 is a description of two-chamber assay structure where the generation of the electroactive species by presence of the analytes (Reaction Chamber) is separated from the detection of the electroactive species.

Redox cycling typically uses two working electrodes, with the potential of one electrode set to oxidize the target molecule (G: Generator), while the second electrode is set to a reducing potential (C: Collector). When the target molecule interacts with the oxidizing electrode it donates an electron, and when it interacts with the reducing electrode it gains the electron back and is able to repeat the process (FIG. 1). This cycling process significantly increases the signal compared to a single working electrode system. Strayer et al. (2012) recently demonstrated this effect by constructing a microfluidic electrode assembly where the spacing between the top and bottom electrodes was on the order of 1 micron (Straver, et al., Lab Chip 12, 1548-1553).

Devices for electrochemical measurement of a concentration of a redox active substance, methods of fabricating the devices, and methods of measuring a concentration of a redox active substance using the devices are provided.

Inexpensive 3D electrodes with high surface area to detection of electrochemical signal in redox cycling can be constructed with carbon matrix (US 2011/0070490 A1). Briefly, in one example, a reactive-ion etching process (RIE) 300, e.g. deep anisotropic inductive coupled plasma etching, is used to pattern 3D structures into a precursor sheet of material that when pyrolyzed transforms into an a lithium intercalating material. The precursor sheet is preferably formed from a polymer or mixture of two or more polymers preferably comprising a polyimide type of polymer. The 3D structure is then converted through pyrolysis into a lithium intercalating structure such as a carbon or carbon containing structure. The resulting carbon containing structure can be used as an electrode for electrochemical applications.

Additionally, polyimide material can be converted into graphite at higher temperatures. Such electrochemical sensor can be used in an assay system that utilize electroactive compounds as tags to detect specific analytes in biological materials.

In one example, protein antigen detection by immunoassay using two separate chambers for the reaction, and detection is shown in FIG. 1. In this example, a specific antibody against protein antigen (10) is bound to a solid surface, where it captures the protein antigen (11) from a sample. Then the second antibody (12) labeled with horseradish peroxidase (HRP) is binds to the captured antigen. Introduction of o-phenylenediamine (OPD) substrate (13) initiate enzymatic reaction between HRP and results in a formation of 2,3-diaminophenazine (DAP) that is electroactive (14). After the reaction, the resulting electroactive DAP is moved into a detection chamber that includes a carbon 3D sensor (15). Inside the sensor a redox cycling is initiated by DAP and through the generator and collector electrodes resulting in an electrical signal that is detected by the sensor. The advantage of this format is that the signal generation is specifically determined by the conversion of OPD to DAP by HRP, and that there will not be non-specific signal generation by unreacted OPD. Another advantage is that one HRP molecule can generate multiple DAP electroactive species that provides additional signal amplification in addition to the redox cycling.

Figure 2:
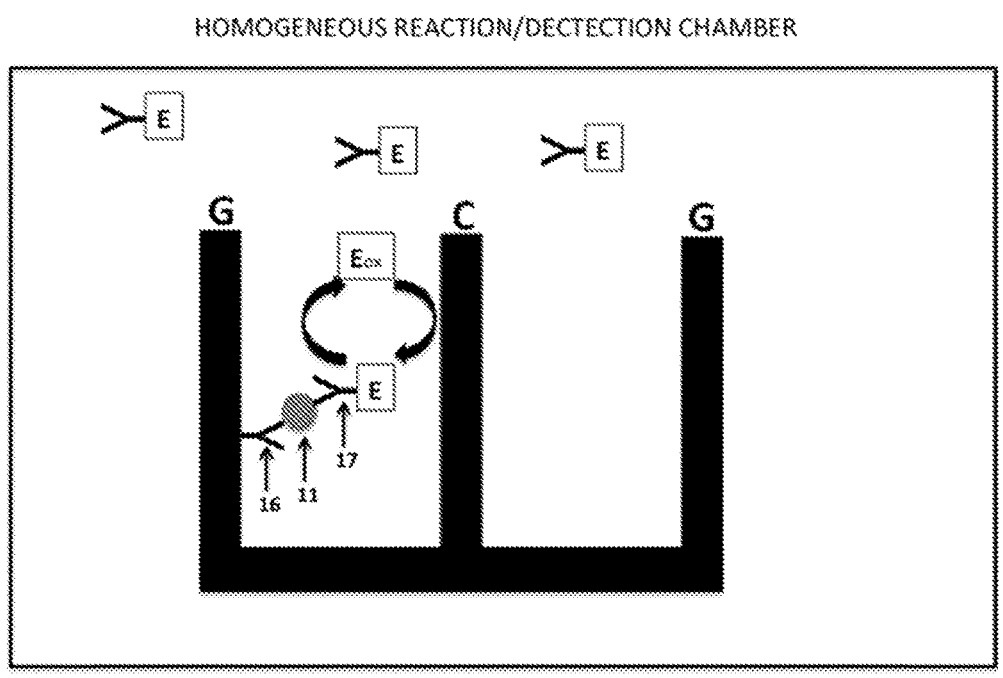
FIG. 2 is a description of one-chamber assay structure where the presence of the analytes is detected directly by the binding of the electroactive species to the close proximity to the sensor.

In another example, protein antigen detection by immunoassay using a single chamber is shown in FIG. 2. In this example, a carbon 3D sensor coated with a specific antibody against the protein analyte (16) is placed inside a chamber with a second antibody against the analyte labeled with an electroactive compound (17), and a sample containing the target analyte (11). The mixture is allowed to form a sandwich structure within the sensor consisting of two antibodies with a target protein in-between. The formation of the sandwich structure brings the electroactive species in close vicinity of the sensor which results in redox amplification signals generated between the generator and collector electrodes. Potential background signals from the unbound detector antibody labeled with an electroactive compound is reduced by sufficiently diluting the reaction so that the chance of unbound detector generating a signal inside the sensor is reduced or eliminated. Another means to reduce the potential background is to constantly flow reagents inside the chamber so that the unbound detector antibody is washed over the sensor without generating a signal, which only the sandwich structure that forms between the antibodies and the analyte, that is physically attached to the sensor, can generate a redox signal. The advantage of this assay structure is that the reaction and detection occurs in a homogeneous mixture which does not require any washing, or reagent transfer steps. The elimination of washing or reagent transfer steps significantly simplifies the assay structure which will result in simpler and less expensive instrument requirements.

In some embodiments, wherein the method for quantitating or detecting the presence or absence of an analyte comprises: adding a sample to an assay structure having at least one electrode and an analyte binding material; allowing an analyte in said sample to bind to said analyte binding material in said assay structure; adding an analyte binding molecule having a tag attached wherein said tags includes an electroactive species capable of generating a current by either accepting or transmitting one or more electrons to the at least one electrode; and measuring a current through said assay structure by means of the at least one electrode within the assay structure thereby quantitating or detecting the presence or absence of the analyte, the tag is reacted with a substrate such that it releases the electroactive species.

Release of the electroactive species may occur by any suitable method. In some embodiments, release of the electroactive species is achieved by reaction, such as but not limited to a change in temperature, change in pH, and/or the addition of an activating compound or enzyme.

In some embodiments, the tag is an alkaline phosphatase, the substrate is 4-aminophenyl phosphate, and the released electroactive species is a p-aminophenol. In some embodiments, the tag is a horseradish peroxidase, the substrate is o-phenylenediamine, and the released electroactive species is a 2,3-diaminophenazine. Further, the tag may be selected from the enzyme group consisting of peroxidase or phosphatase.

The assay structure may employ any suitable analyte binding materials. In some embodiments the analyte binding materials are selected from the group consisting of plastic, metal, carbon or any other solid surfaces. In some embodiments, the analyte binding material may be magnetic. In some embodiments, the analyte binding material may be comprised of beads or particles. In other embodiments, the analyte binding molecule is selected from the group consisting of a secondary antibody, a protein, or a ligand.

In some embodiments, an electrochemical sensor is provided, comprising an electrode assembly which comprises at least two electrodes, one of said electrodes being capable of detecting one or more analyte. The electrode assembly may be further comprised of a working electrode capable of detecting one or more biomarkers for cancer, a counter electrode and a reference electrode.

The electrochemical sensor may have a single working electrode, or alternatively the senor may have one or more electrodes that are a three dimensional electrode. In some embodiments, the three dimensional electrode is comprised of: a base comprising a conductive material, and a plurality of fingers comprising a conductive material, wherein adjacent fingers are in spaced relation and the plurality of fingers extend outwardly from the base, and wherein the base and plurality of fingers are formed from the same conductive precursor material. In some embodiments, the plurality of fingers are bonded to the base with a carbon containing bonding material and the bonding material is formed from the same carbon precursor material as the base and the plurality of fingers.

Any suitable conductive material may be used, such as for example metal, carbon, or plastic.

The sensor may be etched from a single piece of conductive material. The sensor may be formed from a carbon precursor material, and the carbon precursor material may comprise one or more polymers. In some embodiments, the polymer material is a polyimide.

Of particular advantage, the electrochemical sensor may be used in the diagnosis of cancer. In some embodiments, one or more biomarkers for cancer may be detected. In some embodiments, at least one biomarker is selected from Survivin, p26ink4a, HPV E7, HPV E6, Keratin 17, hTERT, and Erk1a.

In some embodiments, an apparatus for detecting one or more biomarkers for cancer is provided, comprising: an electrochemical sensor according to any preceding claim; a housing for the electrochemical sensor; a receiver configured to allow the passage of sample into the housing; and a reader for displaying results produced by the electrochemical sensor.

A method of diagnosing disease is also provided, comprising the steps of: exposing an electrochemical sensor according to any of the above claims to protein samples; applying a potential; measuring a current generated; processing the measured current to determine a concentration of one or more biomarkers for cancer; and determining whether disease is present.

Of further advantage, the various embodiments of the electrochemical sensor described herein may be employed as a kit. For example, in some embodiments, a cancer testing kit comprising the electrochemical sensor is provided. In another embodiment, a pathogen testing kit comprising the electrochemical sensor is provided. In further embodiments, an inflammation testing kit comprising the electrochemical sensor is provided. In even further embodiments, a cardiovascular disease testing kit comprising the electrochemical sensor is provided.

The present invention is not to be limited in scope by the specific embodiments disclosed herein, which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

What is claimed is:

1. A method for processing complex samples and detecting multiple analytes for indication of the presence or absence of disease states comprising:
    adding a sample to an assay structure having a three dimensional electrode assembly and an analyte binding material, the three dimensional electrode assembly further comprising:
        a base comprising a conductive material; and
        a plurality of fingers comprising a conductive material, the plurality of fingers further comprising at least a first electrode set to oxidizing potential and a second electrode set to reducing potential, wherein adjacent fingers are in spaced relation and the plurality of fingers extend outwardly from the base, and wherein the base and plurality of fingers are formed from the same conductive precursor material;
    allowing one or more analytes in said sample to bind to said analyte binding material in said assay structure, wherein the one or more analytes comprise at least one biomarker selected from the group consisting of Survivin, p26ink4a, HPV E7, HPV E6, Keratin 17, hTERT, and Erk1a;
    adding an analyte binding molecule having a tag attached wherein said tags includes an electroactive species capable of generating a current by either accepting or transmitting one or more electrons to the first or second electrode, and wherein said tag is reacted with a substrate such that the tag releases the electroactive species and the tag is selected from the enzyme group consisting of peroxidase or phosphate; and
    measuring a current through said assay structure with the three dimensional electrode assembly within the assay structure and amplifying the current by redox cycling thereby quantitating or detecting the presence or absence of the one or more analytes.

2. The method of claim 1, wherein release of the electroactive species is selected from the reaction consisting of change in temperature, change in pH, and addition of an activating compound or enzyme.

3. The method of claim 1, wherein said tag is an alkaline phosphatase, the substrate is 4-aminophenyl phosphate, and the released electroactive species is a p-aminophenol.

4. The method of claim 1 wherein said tag is a horseradish peroxidase, the substrate is o-phenylenediamine, and the released electroactive species is a 2,3-diaminophenazine.

5. The method of claim 1 wherein the analyte binding materials in said assay structure is selected from the group consisting of plastic, metal, carbon or any other solid surfaces.

6. The method of claim 5, wherein the analyte binding material is magnetic.

7. The method of claim 5, wherein the analyte binding material is beads or particles.

8. The method of claim 1, wherein the analyte binding material comprises an analyte binding molecule selected from the group consisting of a secondary antibody, protein, and ligand.

\* \* \* \* \*